US005587158A

United States Patent [19]
Wall et al.

[11] Patent Number: 5,587,158
[45] Date of Patent: Dec. 24, 1996

[54] BIOLOGICAL CONTROL FOR WEED TREES

[75] Inventors: Ronald Wall; Raghubir Prasad, both of Victoria; Elaine Sela, Shawnigan Lake, all of Canada

[73] Assignee: Minister of Natural Resources, Canadian Forest Service, Hull, Canada

[21] Appl. No.: 411,334

[22] Filed: Mar. 27, 1995

[51] Int. Cl.$^6$ .......................... A01N 25/00; A01N 63/00; C12N 1/00; C12N 1/14

[52] U.S. Cl. .......................... 424/93.5; 424/405; 435/243; 435/254.1; 435/911; 504/116; 504/117

[58] Field of Search .................................. 424/93.5, 405; 435/243, 911, 254.1; 504/116, 117

[56] References Cited

U.S. PATENT DOCUMENTS

| | | | |
|---|---|---|---|
| 5,292,659 | 3/1994 | Cartwright et al. | 435/254.1 |
| 5,391,538 | 2/1995 | Heiny et al. | 504/117 |

OTHER PUBLICATIONS

Tabata et al., Natural Medicines, 48(1) 1994 18–27, abstr.
Tandon, Proc Nat. Acad Sci. India Sect. A Phys Sci., bib.
Spiers et al., Eur J. For Pathol 18(5) 1988 257–78, abst.
Fedorova et al., bib. Mikol Fitopatol 8(2) 1974.
SU Y–C et al, Proc. Nat'l Sci Counc Repub China H(2Pt3) 1980 abst.
Yoshimura et al. Agr. Biol. Chem. 39 (9), 1975, 1789–95.
Yoshida et al., Nippon Kingakukai Kaiho 35 (3) 1994, 173–80, abstr.

*Primary Examiner*—John W. Rollins
*Assistant Examiner*—Deborah K. Ware
*Attorney, Agent, or Firm*—George A. Seaby

[57] ABSTRACT

The common tree patbogen *Chondrostereum purpureum* is a known agent for effective biological control of so-called weed trees, e.g. red alder (*Alnus rubra* Bong). However, the commercial production and application of *C. purpureum* as a biological control has been hindered by the lack of durable and easily produced reproductive structures (spores) and the fragile nature of the fungus mycelium. In accordance with the present invention, a refrigeration storable preparation of the fungus *C. purpureum* includes a culture medium containing 90–95% by weight finely powdered inert material, approximately 3–10% by weight carbohydrates, approximately 0.1–0.3% by weight of a nitrogen source capable of providing approximately 0.01–0.03% by weight nitrogen; and trace amounts of a vitamin, preferably thiamine; sufficient water to establish and promote fungus growth while avoiding free moisture; and live mycelium of the fungus *Chondrostereum purpureum*. Such a preparation can be packaged and stored for up to one year. When mixed with a liquid carrier such as water, the product can be applied to weed trees.

3 Claims, No Drawings

BIOLOGICAL CONTROL FOR WEED TREES

BACKGROUND OF THE INVENTION

1. Field of the Invention

This invention relates to a fungus preparation for control of weed trees.

More specifically the invention relates to a preparation of the fungus *Chondrostereum purpureum*, a method of producing such a preparation and to a method of treating weed trees with the preparation for the biological control of such trees.

2. Discussion of the Prior Art

Some trees in certain areas are considered to be unwanted or weed trees. It is frequently necessary to control the growth of selected tree species or selected trees in industrial right-of-ways and in reforestation areas without using toxic chemical herbicides. The control of red alder (*Alnus rubra*, Bong.) in reforestation areas is expensive in terms of weeding costs and lost growth potential. Other so-called weed trees include aspens (*Populus tremuloides* Michx.), beech (*Fagus grandifolia* Ehrh.), birches (*Betula alleghaniensis* Britt., papyrifera Marsh), maples (*Acer macrophyllum* Pursh., rubrum L), pin cherry (*Prunus pensylvanica* L.f.) and poplars (*Populus balsamifera* L.).

The common tree pathogen and wood rot fungus *Chondrostereum purpureum* (sometimes referred to hereinafter as *C. purpureum*) has been proposed as an effective biological control for the above-listed trees (see Wall, R. E., "The Fungus *Chondrostereum purpureum* as a Silvicide to Control Stump Sprouting in Hardwoods", Northern Journal of Applied Forestry 7:17–19). The fungus can kill meristematic tissues and prevent recovery through wood healing or stump sprouting. Because the fungus can be applied selectively, its use for control of the target trees or species of trees does not threaten the use of the same species for commercial or other purposes. However, the commercial production and application of *C. purpureum* as a biological control has been hindered by the lack of durable and easily produced reproductive structures (spores) and the fragile nature of the fungus mycelium. Actively growing mycelium of *C. purpureum* is a good source of inoculum for treating stumps and tree wounds for biological control However, maceration of the mycelium to facilitate application as a spray drastically reduces its viability. The fungus does not withstand drying, fragmentation and pelletization treatments which have been developed for other microbial products. The fungus has no dormant stage. There is a need for a formulation consisting of the fungus and non-toxic, biodegradable adjuvants. Cultures grown on whole or milled cereal grains are easily contaminated and overgrown by airborne molds. *Chondrostereum purpureum* is easily cultivated and stored on nutrient enriched soil substitutes such as vermiculite, but many such materials are too coarse to be applied as sprays or pastes. Coarse carriers are easily dislodged. Moreover, the unprotected mycelium applied to stumps and wounds is subject to desiccation and damage from ultraviolet radiation during the establishment period.

GENERAL DESCRIPTION OF THE INVENTION

An object of the present invention is to provide a solution to the problems set out above in the form of a preparation of the fungus *Chondrostereum purpureum* which is relatively easy to apply to weed trees and which can be stored for long period of time without substantial deterioration.

Another object is to provide a non-toxic, biodegradable formulation of *Chondrostereum purpureum*.

Another object of the invention is to provide a method of rapidly producing large quantities of a storable preparation of the fungus *Chondrostereum purpureum*.

Yet another object of the invention is to provide a method of treating a weed tree with the fungus *C. purpureum*.

Another object of the invention is to provide a preparation of *Chondrostereum purpureum* which can be applied to target species as a paste or spray using conventional application equipment.

According to one aspect the invention relates to a refrigeration storable preparation of the fungus *Chondrostereum purpureum* comprising:

(a) a culture medium including approximately 90–95% by weight finely powdered inert material, approximately 3–5% by weight digestible carbohydrates, approximately 0.1–1.0% by weight of an organic nitrogen source capable of providing approximately 0.01–0.10% by weight available nitrogen; and trace amounts of vitamin;

(b) sufficient water to maintain living mycelium of the fungus without promoting excessive growth or free moisture; and (c) viable mycelium of *Chondrostereum purpureum* in an amount sufficient to initiate infection of a weed tree.

According to another aspect, the invention relates to a method of producing a refrigeration storable, non-toxic and biodegradable preparation of the fungus *Chondrostereum purpureum* comprising the steps of:

(a) preparing a culture medium including approximately 90–95% by weight finely powdered inert material, approximately 3–5% by weight carbohydrates, approximately 0.1–1.0 % by weight of a nitrogen source capable of providing approximately 0.01–0.10% by weight nitrogen; and trace amounts of vitamin;

(b) mixing said culture medium with sufficient water to establish fungus growth while avoiding free moisture;

(c) inoculating the mixture thus produced with live mycelium of *Chondrostereum purpureum*; and (d) incubating the resulting fungal preparation under conditions suitable to promote the appropriate level of fungus growth.

According to a third aspect, the invention relates to a method of treating a weed tree comprising the steps of:

(a) preparing a culture medium including approximately 90–95% by weight finely powdered inert material, approximately 3–5% by weight carbohydrates, approximately 0.1–1.0% by weight of a nitrogen source capable of providing approximately 0.01–0.10% by weight nitrogen, and trace amounts of vitamin;

(b) mixing said culture medium with sufficient water to establish fungus growth while avoiding free moisture;

(c) inoculating the mixture thus produced with live mycelium of *Chondrostereum purpureum*;

(d) incubating the resulting fungal preparation under conditions suitable to promote substantial fungus growth; and (e) applying the thus produced fungus preparation to the weed tree as an aqueous or vegetable oil paste or suspension.

DETAILED DESCRIPTION OF THE INVENTION

In the research leading up to the present invention, a variety of culture and formulation routines were tried for *C. purpureum*. The formulations were stored in polyethylene bags under three different sets of conditions; room temperature, refrigeration at 4°–6° C. and frozen (–10° C.). Stored formulations were tested periodically for viability by inoculating duplicate malt agar plates with fragments (5–10 mg.) of the formulation and rating the vigour of mycelium outgrowth (recovery rating) of *C. purpureum* when plates were incubated at 20° C. (0=no outgrowth after 2 weeks incubation, 1=no growth at 5 days but some growth at 14 days, 2=no growth at 3 days but some growth at 5 days, 3=radial growth of 1–5 mm after 3 days incubation, 4=radial growth of 6–10 mm after 3 days incubation, 5=radial growth greater than 20 mm after 3 days incubation). Formulations from which vigorous mycelium could be recovered after storage were further tested for infectivity by applying them in an aqueous paste or spray to freshly cut stem sections of red alder, 4–7 cm diameter by 4–6 cm long, incubating them in a shallow pan of water under normal laboratory conditions for two weeks, and splitting them open to culture the fungus from chips removed aseptically from the outer xylem 1–2 cm below the inoculated surface. Infectivity was rated by mycelial outgrowth from the chips according to the above 0–5 rating system.

Promising formulations were tested for herbicidal efficacy in small scale field tests by applying them in aqueous or vegetable oil suspensions to cut stumps of red alder and later evaluation (against controls consisting of sterile formulation) for mortality of stump sprouts and fructification of *C. purpureum*. All infectivity and efficacy tests were replicated ten times in randomized plots and treatment effects compared through analyses of variance and Duncan's Multiple Range test.

Viable mycelium of *C. purpureum* could readily be produced in liquid or solid culture using a wide variety of plant products, e.g. malt extract, potato extract, cereal grains such as corn, oats and rice, wheat bran and autoclaved stem tissues of woody plants. When grown on nutrient rich plant products such as cereal grains it was necessary to maintain the cultures in sterile condition or air-dry them quickly to prevent contamination by air-borne molds. However, air-dried cultures lost their viability. Storage of moist sterile cultures under refrigeration (4°–6° C.) maintained viability for at least one year. These cultures provided suitable inoculum if applied to stumps or wounds as coarse pastes and protected in some manner from drying and sunlight [applying in a vegetable or mineral oil slurry or covering with aluminum foil, plastic or Parafilm M (trademark—American National Can Co., Greenwich, Conn.)].

Luxuriant mycelial growth from nutrient rich cultures were macerated into aqueous suspensions in a blender to provide flowable preparations that could be applied in a plastic squeeze bottle or sprayer. Small scale field trials on red alder and big leaf maple with such suspensions did not give consistent results. Viability tests indicated a sharp reduction in recovery of vigorous mycelia growth as a result of maceration as illustrated in Table 1.

TABLE 1

| Type of culture and maceration medium | Mean recovery rating* Duration of maceration, minutes: | | | | |
|---|---|---|---|---|---|
| | 0 | 0.5 | 1 | 2 | 3 |
| Malt agar | | | | | |
| Distilled water | 4.0 | 2.0 | 1.7 | 2.0 | 2.0 |
| Vegetable oil | 4.0 | 0.5 | 0.0 | 0.0 | 0.0 |
| Whole corn | | | | | |
| Distilled water | 3.3 | 0.0 | 0.7 | 0.7 | 0.0 |
| Vegetable oil | 3.3 | 1.7 | 0.7 | 2.0 | 1.7 |

*0 = no recovery after 2 weeks,
1 — some growth after 2 weeks,
2 = some growth after 5 days,
3 = radial growth of 1–5 mm after 3 days,
4 = radial growth of 6–10 mm after 3 days and
5 — radial growth of *C. purpureum* mycelium of more than 10 mm after 3 days incubation at 20° C.

Mycelial cultures were formulated on 20 separate occasions as invert emulsions and pelleted in alginate (as per Connick et al "An Improved Invert Emulsion with High Water Retention for Mycoherbicide Delivery", Weed Technology 5:442–444, 1991). An example of this type of formulation is as follows:

Oil Phase

| Unrefined corn oil | 175 ml |
|---|---|
| Light mineral oil | 60 ml |
| Lanolin | 30 ml (28 g) |
| Paraffin (sealing wax) | 25 ml (22 g) |

Ingredients were mixed and gently heated to melt the paraffin.

Aqueous Phase

| Sodium alginate | 4 g |
|---|---|
| Kaolin | 30 g |
| Distilled water | 300 ml |
| Streptomycin | 120 ppm |

Mycelium of *C. purpureum* (20–15 g wet weight) was obtained from broth cultures by filtration and mixed with the aqueous phase, which was then added dropwise to 0.25M calcium chloride solution on a stirrer. The resulting pellets were washed in distilled water and mixed with 100 ml of the oil phase. Finely powdered silica (80 g) was then added to this mixture and the preparation of air-dried by spreading on aluminum foil.

None of these formulations remained viable for periods longer than 1 month under any of the storage regimes.

It became apparent that the production of mycelium (culture), formulation and storage phases should be continuous, with the product kept in a moist, growing condition and maintained as pure cultures (protected from airborne contaminants) until field application. Cultures were grown in autoclaveable plastic bags on sterile vermiculite containing small quantities of macerated cereal grains and pectin, prepared as follows:

A mixture of 10 g wheat bran, 10 g oat kernels, 10 g corn kernels and 10 g safflower seed were soaked over-night in 1 liter of distilled water, macerated in a blender, and 10 g of pectin added to slurry. The slurry was then autoclaved, inoculated with *C. purpureum*, and incubated at room temperature for 9 days. Aeration was provided by a magnetic stirrer. Aliquots (100 ml) of this slurry were aseptically added to autoclaved plastic bags each containing 100 g of sterile vermiculite. The bags were incubated at room temperature for 4 weeks, with twice-weekly agitation of the contents of each bag to promote uniform growth, and then stored at room temperature, refrigerated (4°–6° C.) or frozen (−10° C.).

The vermiculite formulation stored at room temperature remained viable for 3 months (recovery rating of 5) but was no longer viable after 5 months. Frozen formulation was viable after 8 months storage (recovery rating of 3) but was no longer viable after 10 months. However, formulation stored at 4°–6° C. has remained viable to time of writing (20 months with a recovery rating of 3).

The refrigerated vermiculite formulation was used in a small scale field test after 3 months storage. The formulation was mixed with distilled water or vegetable oil to form smooth pastes. To half of each of the water or oil preparations, finely powdered cellulose (10 g added to 50 g formulation) was incorporated as an adhesive. Controls consisted of sterile vermiculite moistened with water or oil. The six preparations were applied with a spatula to freshly cut stumps of red alder saplings (4–6 cm diameter), 10 stumps per treatment in a randomized block in a Douglas-fir plantation near Victoria, British Columbia. Results are presented in Table 2.

TABLE 2

| Treatment | Sprouts per stump* | Stumps with sprouts* >20 cm high | Stumps with sprouts* Total | Fruiting bodies (cm$^2$)** |
|---|---|---|---|---|
| Water suspension | | | | |
| No adhesive | 0.8 | 1 | 2 | 211 |
| Cellulose added | 0.9 | 0 | 3 | 213 |
| Oil suspension | | | | |
| No adhesive | 1.4 | 0 | 0 | 168 |
| Cellulose added | 2.0 | 0 | 0 | 296 |
| Controls | | | | |
| Water suspension | 5.1 | 2 | 8 | 55 |
| Oil suspension | 4.0 | 2 | 4 | 70 |

*Based on a total of 10 stumps; data collected 9 months after treatment. For the first column (sprouts/stump), the combined treatments are significantly different from the combined controls at p = 0.01.
**Mean area of stump surface occupied by fruiting bodies of *C. purpureum*; data collected 14 months after treatment.

It was therefore very clear that maintenance of a continuous and closed pure culture system throughout the production and storage phases was a valuable concept in the development of bioherbicides based on fragile mycelia such as *C. purpureum*. Also, having an inert ingredient such as vermiculite as the major component throughout the production and storage phases was important in that it provided a base for the development of adequate and intact mycelial growth by the time of field application but did not support the production of luxuriant mycelial growth which would interfere with field application. However, the vermiculite formulation was difficult to apply since the coarse granules did not form a smooth paste when moistened although the addition of powdered cellulose helped to improve its consistency. Application of this formulation as a spray was not possible.

On the bases of the above observations, powdered inert ingredients were considered as carriers and soluble or finely pulverized materials were considered as nutrient sources. A culture medium/formulation of the following composition was prepared:

750 g powdered talc, 200 g kaolin, 25 g corn starch, 10 g pectin, 10 g monosodium glutamate, 2 g monopotassium phosphate and 3 g yeast extract were mixed and sterilized in autoclaveable plastic bags and 200 ml of a 2 day old malt broth culture suspension aseptically added. The bags were incubated at room temperature and agitated twice weekly to promote uniform growth. After four weeks, the bags were refrigerated (4°–6° C.).

The above formulation was viable at the time of writing (5 months storage with recovery rating of 5). An aqueous slurry of the formulation was placed on alder stem sections which were split open and cultured two weeks later, yielding cultures of *C. purpureum* (recovery rating 2–4).

The formulation was applied to freshly cut stumps of red alder saplings as a spray (50 g formulation+20 g powdered cellulose+100 ml distilled water+200 ml vegetable oil) in July of 1994. Twelve inoculated stumps sampled in November and cultured on malt agar yielded *C. purpureum* (recovery ratings of 2–4 in 27 out of 38 isolation attempts), while six control stumps yielded no *C. purpureum* in isolation attempts.

In September of 1994, stumps of 300 red alder and 200 big leaf maple were treated with a formulation of the same composition in a paste suspension prepared at the field site as follows: 1000 g formulation, 1200 ml of sterile 1% sucrose in water, 400 ml vegetable oil, the yolk from four eggs and 240 g powdered cellulose stirred vigorously to form a uniform suspension. At the termination of this test, extra treatments were performed on 6 red alder and 6 black cottonwood stumps, which were harvested, dissected and cultured two months later. Thirteen out of 15 isolation attempts from red alder and 10 out of 11 isolation attempts from black cottonwood yielded *C. purpureum* (recovery ratings of 2–3 in each case).

The prescribed production, storage and application processes for a formulation of *Chondrostereum purpureum* and similar mycelial biologicals are as follows:

I Prepare batches of culture medium containing the following ingredients in the following proportions by weight:

| | |
|---|---|
| Inert ingredient | 90–95% |
| finely powdered talc, clay mineral or other non-toxic, naturally occurring substance with low levels of biologically available nutrients | |
| Carbohydrate | 3–5% |
| starch, pectin or combination or pulverized plant product containing polysaccharides | |
| Nitrogen source | 0.1–1.0% |
| an organic form of nitrogen containing 5–20% available N. Preferred nitrogen sources are glutamine, L-glutamic acid, valine, casein hydrolysate or other non-toxic amino acid mixtures of peptides (Jennison et al, Physiology of Wood-rotting Basidiomycetes I. Growth and Nutrition in Submerged Culture in Synthetic Media, Mycologia 47: 275–304, 1955) | |
| Vitamin source | 0.05–0.1% |
| a naturally occurring organic product containing the vitamin thiamine, e.g. yeast extract | |

II Sterilize in gas permeable containers suitable for incubation, storage, transportation to field locations, the addition of other ingredients under aseptic conditions, and mixing of ingredients without contamination by other microorganisms.

III Aseptically add to the containers a liquid culture or macerated solid culture of *Chondrostereum purpureum* or the desired biological agent that contains actively growing but macroscopically invisible particles of the biological control agent and sufficient water to allow further growth but not restrict aeration and further mixing of contents. This moisture level will usually be 15–25% of the dry weight of the formulation.

IV Incubate the containers containing the actively growing cultures at 15°–25° C. for 1–4 weeks in the case of *C. purpureum* or under conditions suitable for the biological control agent. The resulting active ingredient level (dry weight of live mycelium of *C. purpureum* or similar mycelial biological) should be 1–5% based on the dry weight of the formulation.

V Store containers at 1°–6° C. under reasonably dry conditions.

VI Transport to place of application under dry conditions at temperatures not exceeding 30° C.

VII Apply to target species as an aqueous or oil suspension (paste of spray) or as an emulsion containing a non-toxic naturally occurring emulsifying agent. Sucrose, dextrose or other metabolizable sugar may be added as an energy source at a level not exceeding 5% of the final suspension. Powdered cellulose or other naturally occurring, non-toxic adhesive may also be added at whatever level is necessary to provide improved adhesiveness and rain-fastness.

Naturally occurring, non-toxic, and biodegradable organic products containing the ingredients listed in I can be substituted for any of the carbohydrate, nitrogen or vitamin sources and possibly even the inert ingredient provided that the inert ingredient is not rapidly metabolized by the biological control agent and does not appreciably alter the carbon:nitrogen ratio.

A preferred formulation, based on laboratory and field experiments in a research establishment, includes the following ingredients in the proportions listed.

| | |
|---|---|
| Talc (powder) | 750 |
| Kaolin | 200 |
| Starch | 25 |
| Pectin | 10 |
| Monosodium glutamate | 10 |
| Monopotassium phosphate | 2 |
| Yeast extract | 3 |

The dry fermentation medium is packaged in gas permeable containers and sterilized.

Fragmented mycelium of the fungus, *C. purpureum* or similar biological agent is initially cultured for 1–3 days in 1–3% malt extract broth or similar liquid nutrient medium in an aerated liquid fermentation system and aseptically inoculated into the dry fermentation medium in sufficient quantity to provide a uniform distribution of fungus inoculum and provide adequate moisture for fungus growth. Fragments of the inoculum should be invisible macroscopically at the time of inoculation. This step provides for rapid scale-up of cultures and reduced incubation time.

Containers of the growing cultures are incubated for 1–4 weeks under normal room conditions, i.e. darkness or diffuse light with temperatures not exceeding 25° C. Containers should be agitated once or twice weekly, or more often if desired, to promote growth and maintain even distribution of mycelia. Sample containers are checked for viability by aseptically placing 5–10 mg quantities of formulation on malt or similar nutrient agar and examining for mycelial growth of the fungus after 3 days incubation at 20° C.

The containers may be stored in clean, dry refrigerators or cold storage rooms at temperatures of 1°–6° C. until needed for use. Samples should be checked periodically for viability and containers with noticeably reduced viability discarded. During transportation, warm temperatures (above 30° C.) and wet conditions should be avoided.

Within a few hours before application, liquid diluents (water, vegetable or mineral oil, oil-water emulsions), energy sources (sugars), and adhesives (e.g. powdered cellulose) may be added and thoroughly mixed with the formulation by stirring or gentle agitation. The formulation may be applied as a smooth paste, flowable suspension or spray using equipment that will allow free flow of loose wefts of mycelium.

We claim:

1. A refrigeration storable preparation of *Chondrostereum purpureum* fungus for the control of weed trees selected from the group consisting of aspens, beech, birches, maples, pin cherry and poplars comprising:

(a) a dry culture medium consisting of 90–95% by weight finely powdered inert material, approximately 3–5% by weight digestible carbohydrates, approximately 0.1–1.0% by weight of an organic nitrogen source capable of providing approximately 0.01–0.10% by weight available nitrogen; and 0.5–1% by weight vitamin;

(b) water in an amount to maintain a moisture level of 15–25% by weight based on the dry weight of the culture medium for maintaining living mycelium of the fungus without promoting excessive growth or free moisture; and (c) viable mycelium of *Chondrostereum purpureum* in an amount of 1–5% by weight based on the dry weight of the culture medium.

2. The refrigeration storable preparation of claim 1, wherein the culture medium includes the following:

| Ingredient | % by Weight |
|---|---|
| Talc [(powder)] | 75.0 |
| Kaolin | 20.0 |
| Starch | 2.5 |
| Pectin | 1.0 |
| Monosodium glutamate | 1.0 |
| Monopotassium phosphate | 0.2 |
| Yeast extract | 0.3. |

3. The refrigeration storable preparation according to claim 1, wherein the culture medium includes powdered talc and a clay mineral as the inert ingredient, starch and pectin as the carbohydrate and monosodium glutamate as the nitrogen source.

\* \* \* \* \*